United States Patent
Schröck et al.

(10) Patent No.: US 10,610,309 B2
(45) Date of Patent: Apr. 7, 2020

(54) DENTAL SYSTEM

(71) Applicant: W&H Dentalwerk Bürmoos GmbH, Bürmoos (AT)

(72) Inventors: Rainer Schröck, Bürmoos (AT); Wolfgang Tannebaum, Weiden (AT)

(73) Assignee: W&H Dentalwerk Bürmoos GmbH, Bürmoos (AT)

(*) Notice: Subject to any disclaimer, the term of this patent is extended or adjusted under 35 U.S.C. 154(b) by 29 days.

(21) Appl. No.: 15/257,724

(22) Filed: Sep. 6, 2016

(65) Prior Publication Data

US 2016/0367326 A1     Dec. 22, 2016

Related U.S. Application Data

(63) Continuation of application No. PCT/EP2015/054692, filed on Mar. 6, 2015.

(30) Foreign Application Priority Data

Mar. 6, 2014   (EP) .................................... 14157978

(51) Int. Cl.
*A61B 34/00* (2016.01)
*H04B 13/00* (2006.01)
(Continued)

(52) U.S. Cl.
CPC .............. *A61B 34/25* (2016.02); *A61B 18/00* (2013.01); *A61B 90/98* (2016.02); *A61C 1/0007* (2013.01);
(Continued)

(58) Field of Classification Search
CPC ......... A61C 3/00; A61C 3/0025; A61C 1/007; A61C 1/0005; A61C 1/0023; A61C 3/025;
(Continued)

(56) References Cited

U.S. PATENT DOCUMENTS

| | | | |
|---|---|---|---|
| 3,753,434 A | | 8/1973 | Pike et al. |
| 5,395,240 A | * | 3/1995 | Paschke ................. A61C 17/20 433/119 |

(Continued)

FOREIGN PATENT DOCUMENTS

| | | |
|---|---|---|
| DE | 10201215365 | 12/2013 |
| EP | 0843425 | 5/1998 |

(Continued)

OTHER PUBLICATIONS

International Search Report for PCT/EP2015/054692 (dated May 18, 2015).

*Primary Examiner* — Sean M Michalski
*Assistant Examiner* — Shannel N Wright
(74) *Attorney, Agent, or Firm* — Klarquist Sparkman, LLP (57) ABSTRACT

A medical or dental system with at least one first transmitting and/or receiving unit and at least one second transmitting and/or receiving unit, wherein the at least two transmitting and/or receiving units are designed for the capacitive coupling of electric signals into and/or out of a human body, so that an electric path which extends through the human body of the user and/or of the person to be treated can be established for the transmission of electric signals between the at least one first transmitting and/or receiving unit and the at least one second transmitting and/or receiving unit, in order to transmit data between the at least two transmitting and/or receiving units.

21 Claims, 3 Drawing Sheets

(51) Int. Cl.
*A61C 1/00* (2006.01)
*A61B 18/00* (2006.01)
*A61C 17/02* (2006.01)
*A61B 90/98* (2016.01)
*A61C 3/025* (2006.01)
*A61B 17/00* (2006.01)
*A61N 5/06* (2006.01)

(52) U.S. Cl.
CPC ............ *A61C 1/0015* (2013.01); *A61C 3/025* (2013.01); *A61C 17/0202* (2013.01); *H04B 13/005* (2013.01); *A61B 2017/00221* (2013.01); *A61B 2034/258* (2016.02); *A61B 2560/0214* (2013.01); *A61B 2562/164* (2013.01); *A61B 2562/166* (2013.01); *A61N 2005/0606* (2013.01)

(58) Field of Classification Search
CPC ..... A61C 19/002; A61B 5/0028; A61B 90/70; A61B 90/90–98; A61B 90/92–98; A61B 2562/164; A61B 2562/166; A61B 34/25; A61B 90/98; A61B 18/00; H04B 13/005; B08B 13/00; G16H 40/63; A61L 2202/14; A61L 2202/16; A61L 2/02; A61L 2/04; A61L 2/07; A61L 2/24
USPC ......... 340/5.6–5.67, 10.1–10.6; 422/26, 105, 422/292, 295, 298, 299
See application file for complete search history.

(56) References Cited

U.S. PATENT DOCUMENTS

| | | | | |
|---|---|---|---|---|
| 8,812,368 | B1* | 8/2014 | Gazdzinski | A61B 1/00016 705/21 |
| 9,211,055 | B2* | 12/2015 | Takenaka | A61B 1/041 |
| 2002/0190689 | A1* | 12/2002 | Nakamura | G04C 10/00 320/102 |
| 2004/0209223 | A1* | 10/2004 | Beier | A61B 17/1626 433/99 |
| 2006/0140139 | A1* | 6/2006 | DiSilvestro | A61B 5/0028 370/310 |
| 2007/0136964 | A1* | 6/2007 | Dawley | A61C 17/221 15/22.1 |
| 2007/0160494 | A1* | 7/2007 | Sands | A61L 2/07 422/26 |
| 2007/0190509 | A1* | 8/2007 | Kim | A46B 15/0002 434/263 |
| 2008/0120137 | A1* | 5/2008 | Nyholm | G16H 10/60 705/3 |
| 2009/0149722 | A1* | 6/2009 | Abolfathi | A61B 5/0002 600/301 |
| 2009/0270032 | A1* | 10/2009 | Kassayan | H04B 13/005 455/41.1 |
| 2010/0071736 | A1* | 3/2010 | Watanabe | A61B 1/00006 134/56 R |
| 2010/0249509 | A1* | 9/2010 | Yoshizawa | A61B 1/041 600/118 |
| 2011/0022025 | A1* | 1/2011 | Savoie | A61M 5/14248 604/500 |
| 2011/0097248 | A1* | 4/2011 | Tomita | A61B 1/00059 422/292 |
| 2013/0146108 | A1* | 6/2013 | Suzuki | A61B 1/123 134/113 |
| 2014/0080429 | A1* | 3/2014 | Ohishi | H04B 13/005 455/90.2 |
| 2014/0206976 | A1* | 7/2014 | Thompson | A61B 5/0006 600/391 |
| 2014/0310900 | A1* | 10/2014 | Curry | A46B 9/04 15/167.1 |
| 2015/0088538 | A1* | 3/2015 | Dykes | G16H 50/20 705/2 |
| 2015/0199487 | A1* | 7/2015 | Grauds | A61L 2/10 235/375 |
| 2015/0237461 | A1* | 8/2015 | Goyal | H04W 4/008 455/41.2 |
| 2015/0282884 | A1* | 10/2015 | Wimmer | A61C 19/002 422/292 |
| 2016/0015493 | A1* | 1/2016 | Ertl | A61B 6/145 433/215 |
| 2016/0125678 | A1* | 5/2016 | Coggins | A61B 5/082 340/5.65 |
| 2016/0211822 | A1* | 7/2016 | Weithmann | A61B 6/56 |
| 2016/0338635 | A1* | 11/2016 | Johnson | A61B 5/4547 |
| 2017/0207861 | A1* | 7/2017 | Hyoung | H04W 4/80 |
| 2018/0052454 | A1* | 2/2018 | Magno | A61C 19/002 |

FOREIGN PATENT DOCUMENTS

| | | |
|---|---|---|
| EP | 1187375 | 3/2002 |
| EP | 1392193 | 12/2009 |
| JP | H11509380 | 8/1999 |
| JP | 2003245251 | 9/2003 |
| JP | 2005-521162 | 7/2005 |
| JP | 2010200993 | 9/2010 |
| JP | 2010200993 A * | 9/2010 |
| JP | 2013-186852 | 9/2013 |
| JP | WO2013/115392 | 5/2015 |

* cited by examiner

DENTAL SYSTEM

CROSS REFERENCE TO RELATED APPLICATION

This application is a U.S. bypass continuation application of International Application No. PCT/EP2015/054692, filed Mar. 6, 2015, which in turn claims priority from pending European Patent Application No. EP 14157978.9, filed Mar. 6, 2014, which are incorporated herein by reference.

BACKGROUND

Field

The present invention relates to a medical or dental system with at least a first transmitting and/or receiving unit and at least a second transmitting and/or receiving unit, as well as to a method for transmitting electrical signals and/or data between the at least first transmitting and/or receiving unit and the at least second transmitting and/or receiving unit of the medical or dental system.

Description of Prior Art

Such medical or in particular dental systems preferably are used for the processing of human or animal tissues. To this end, they preferably comprise at least one medical, in particular a dental, straight handpiece or contra-angled handpiece, a drive unit and/or a control unit which is or can be connected to the straight handpiece or contra-angled handpiece, as well as at least one accessory designed for the operation with the straight handpiece or contra-angled handpiece and/or the drive unit and/or control unit.

The at least one straight handpiece or contra-angled handpiece is preferably designed to drive a tool which has an effect or works on a treatment site. The tool preferably is set in motion by means of an electric motor, a pneumatic drive, or a piezo drive, which preferably is located in the straight handpiece or contra-angled handpiece or is connected thereto, in particular by means of a coupling device. Furthermore, the at least one straight handpiece or contra-angled handpiece can be designed to dispense radiation, fluids, energy, abrasive media, and/or to provide measurement data.

To drive and/or control the medical straight handpiece or contra-angled handpiece, it is connected to the drive unit and/or control unit, preferably by means of a supply line. The drive unit and/or control unit provides the working media needed for the medical straight handpiece or contra-angled handpiece and/or tool, such as for example spray air and/or spray water for cooling, drive fluid, in particular compressed air, radiation or electrical energy to supply the electrical components located in the straight handpiece or contra-angled handpiece, such as for example one or more light-emitting diodes to illuminate treatment sites, sensors or electrical memories to store data, preferably instrument-related data.

Furthermore, the medical systems preferably comprise at least one accessory designed for the operation with the straight handpiece or contra-angled handpiece and/or for the operation with the drive unit and/or control unit. Examples thereof include: Instrument holders for the storage and support of the medical straight handpieces or contra-angled handpieces or of tools, glasses, especially protective goggles or filter glasses to detect an anomaly on a tooth, hand mirrors, foot pedals to actuate the drive unit and/or control unit, display elements which are connected to the drive unit and/or control unit by cables or in a wireless manner, or means to identify the user, such as for example magnetic cards or chip cards.

The user has processing devices available for the processing, in particular the cleaning, disinfecting, and/or sterilizing of the at least one medical, in particular dental, straight handpiece or contra-angled handpiece as well as for the processing of the accessories of the medical system. These sterilizers, autoclaves or thermal disinfection units direct at least one operating medium into a processing chamber, in which the at least one medical, in particular dental, straight handpiece or contra-angled handpiece or accessory is held, preferably by a processing holder, or directly pass the medium to the at least one medical straight handpiece or contra-angled handpiece. As the operating medium, preferably fluids are used, such as for example hot water or vapors, in particular saturated steam.

It is known from the prior art to provide the at least one straight handpiece or contra-angled handpiece and/or accessory of the medical system with an encoding in order to supply the working media of the drive unit and/or control unit and/or the operating media of the processing device to the straight handpiece or contra-angled handpiece automatically, depending on the straight handpiece or contra-angled handpiece or accessory of the medical system which is connected through the supply hose to the drive unit and/or control unit or which is located in the processing device. To this end, in particular the encoding comprises identification data, such as for example a serial number, which can be read by the drive unit and/or control unit and/or by the processing device by means of a reading device.

Such a medical, in particular a dental, system is known from EP 1 392 193 B1.

This known medical system comprises a supply unit for supplying at least one medical straight handpiece or contra-angled handpiece with media, in particular with water, compressed air, or light, wherein a supply line runs from the supply unit, at the end of which a coupling part, which can be coupled to a corresponding coupling part of the straight handpiece or contra-angled handpiece, is disposed. A memory element for identification data is provided in the interior of the straight handpiece or contra-angled handpiece which is accessible to the corresponding coupling part of the supply line. Reading the memory element, in particular the transmission of data from the straight handpiece or contra-angled handpiece to the supply unit, is achieved either by mechanical contacting using electrical contacts in the two coupling parts or by wireless contacting by means of two transponders.

Furthermore, the known medical system comprises a processing device with at least one coupling part which can also be coupled to the corresponding coupling part of the straight handpiece or contra-angled handpiece. Reading the memory element in the straight handpiece or contra-angled handpiece, in this case, also takes place by means of a mechanical contacting using electrical contacts or by means of a wireless contacting using two transponders located in the coupling area of the two coupling parts.

A disadvantage of this configuration of the medical system is the transmission of electrical signals, in particular data, between the straight handpiece or contra-angled handpiece and the supply unit and/or the processing device. The transmission of signals and/or data is possible only in a coupled state of the straight handpiece or contra-angled handpiece with the supply unit and/or with the processing device. In particular, in the case of hardwired transmission of signals using electrical contacts, the coupling parts of the straight handpiece or contra-angled handpiece, the supply unit, and/or the processing device must be connected with each other.

But also when using transponders for wireless transmission, which have transmitting and/or receiving coils for the transmitting and/or receiving of signals, coupling of both coupling parts is required, because of the low transmitting and/or receiving power of the coils due to the small size of the transmitting and/or receiving coils and because of the metallic materials in the components of the medical system, in particular in their coupling parts.

SUMMARY

It is thus an object to create a medical or dental system which makes it possible to ensure the secure transmission of electrical signals and/or data between a first transmitting and/or receiving unit and a second transmitting and/or receiving unit. In particular, it is an object of the invention to guarantee the secure transmission of electrical signals even when the components of the medical system are not connected directly with one another.

This objective is accomplished by a medical or dental system which comprises at least a first transmitting and/or receiving unit and at least a second transmitting and/or receiving unit, wherein the at least two transmitting and/or receiving units are designed for the capacitive coupling of electrical signals into and/or out of a human body, so that an electrical path for the transmission of electrical signals between the at least one first transmitting and/or receiving unit and the at least one second transmitting and/or receiving unit, which extends through the human body of the user and/or the person to be treated, can be established in order to transmit data between the at least two transmitting and/or receiving units.

According to a preferred embodiment, the at least one first transmitting and/or receiving unit and the at least one second transmitting and/or receiving unit each comprises at least one printed circuit board for generating and/or receiving electromagnetic fields which can be capacitively coupled into and/or coupled out of the human body. The least one printed circuit board preferably comprises an electrically insulated base body with at least one electrical strip conductor. The base body preferably is formed by a flexible carrier material, preferably by a carrier film.

The capacitive coupling of the electrical signals and/or data, in particular of the electromagnetic fields, into and/or out of the human body of the user and/or of the person to be treated preferably takes place by contacting the human body with the printed circuit board. According to another preferred embodiment, the coupling of the electromagnetic fields into and/or out of the human body takes place without contact.

To supply the printed circuit board with electrical energy and to emit electrical signals, the at least one first transmitting and/or receiving unit and/or the at least one second transmitting and/or receiving unit preferably comprise at least two electrical contacts or at least one energy storage system for electrical energy and at least a memory unit to store and/or output data.

Furthermore, the at least one first transmitting and/or receiving unit and/or the at least one second transmitting and/or receiving unit are each disposed in a housing, the housing being designed in such a way that the functionality of the first or second transmitting and/or receiving unit disposed in the housing can be maintained even after multiple cleaning, care, and/or sterilization processes. The housing preferably is made of a magnetic and electrically non-conductive material, in particular of plastic, glass, or ceramic, and comprises a holding device, in particular a thread, a clip, a clamp, and/or another form of retaining element, so that the at least one first transmitting and/or receiving unit and/or the at least one second transmitting and/or receiving unit can be disconnected from the medical system.

According to another embodiment of the medical or dental system, the at least one first transmitting and/or receiving unit and/or the at least one second transmitting and/or receiving unit are disposed in or on a medical or dental straight handpiece or contra-angled handpiece which is designed to drive a tool which works on a treatment site and/or to emit radiation, fluids, energy, and/or abrasive media and/or to provide measurement data, and/or in or at a drive unit and/or control unit, which is connected to or can be connected to a straight handpiece or contra-angled handpiece for the purpose of driving and/or controlling the at least one straight handpiece or contra-angled handpiece and/or in or on at least one accessory designed for the operation with the straight handpiece or contra-angled handpiece and/or with the drive unit and/or control unit in order to transmit data between the straight handpiece or contra-angled handpiece and/or the drive unit and/or control unit and/or the accessory.

The at least one first transmitting and/or receiving unit or the at least one second transmitting and/or receiving unit is preferably disposed in or at a handle and/or holding part of the straight handpiece or contra-angled handpiece, the drive unit and/or control unit, and/or the accessory. Alternatively, the at least one first transmitting and/or receiving unit or the at least one second transmitting and/or receiving unit is preferably positioned in or at an actuating and/or operating element of the straight handpiece or contra-angled handpiece, the drive unit and/or control unit, and/or the accessory, so that the at least two transmitting and/or receiving units can be capacitively coupled with a user and/or a person to be treated.

According to a further embodiment of the medical or dental system, the at least one first transmitting and/or receiving unit and/or the at least one second transmitting and/or receiving unit are disposed in or at a medical or dental processing device and/or in or at an accessory designed for operating with the processing device.

In this embodiment as well, the at least one first transmitting and/or receiving unit or the at least one second transmitting and/or receiving unit is preferably disposed in or at an actuating and/or operating element or in or at a handle part or gripping part of the processing device or of the accessory for the processing device.

According to an embodiment of a method for the transmission of electrical signals and/or data between at least one first transmitting and/or receiving unit and at least one second transmitting and/or receiving unit of a medical or dental system, the transmission of the electrical signals and/or data takes place by means of: providing at least one first transmitting and/or receiving unit and at least one second transmitting and/or receiving unit which are designed to capacitively couple electrical signals into and/or out of a human body; capacitively coupling the at least two transmitting and/or receiving units with the human body of the user and/or of the person to be treated; establishing an electrical path between the at least one first transmitting and/or receiving unit and the at least one second transmitting and/or receiving unit, which extends through the human body of the user and/or of the person to be treated; and transmitting the electrical signals between the at least two transmitting and/or receiving units.

The present medical or dental system is distinguished by a series of significant advantages.

The medical, in particular dental system in in particular permits signals and/or data to be transmitted between the at least one first transmitting and/or receiving unit and the at least one second transmitting and/or receiving unit without these having to be connected and/or coupled to one another directly. Thus signals and/or data can be transmitted through an electrical path extending through the human body of the user and/or of the person to be treated between components of the medical, in particular dental system, which are at a distance from one another, in particular between the straight handpiece or contra-angled handpiece, the drive unit and/or control unit, the processing device, and/or the accessory for the several components.

Furthermore, the medical, in particular dental system can ensure the secure transmission of signals and/or data between the at least one first transmitting and/or receiving unit and the at least one second transmitting and/or receiving unit even when the at least two transmitting and/or receiving units of the medical system are not coupled directly to one another. The use of the human body of the user and/or of the person to be treated as an electrical path for the transmission of electrical signals and/or data prevents the risk of endangering the signal and/or data transfer. In the case of an inductive energy and/or data transfer, as is known from the prior art, the signal and/or data transfer can be disturbed by electrical counterfields generated by metallic components in the vicinity of the transmitting and/or receiving coils.

The invention will be explained below on the basis of several embodiments and in connection with the attached drawings.

DETAILED DESCRIPTION

Figure 1:
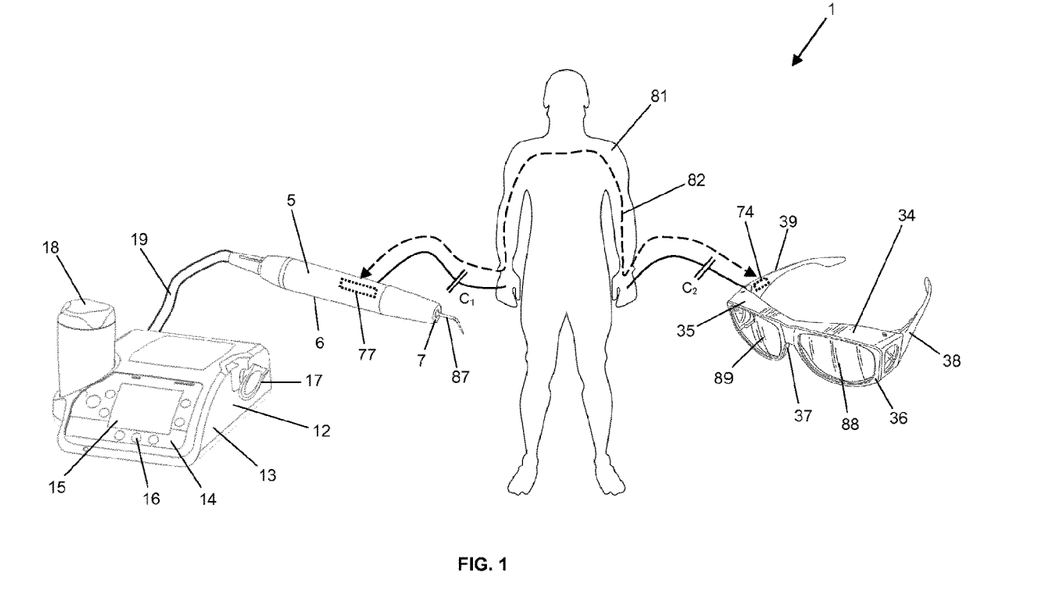
FIG. 1 shows a first embodiment of the medical or dental system with a drive unit and/or control unit, a medical or dental handpiece, and an accessory for the operation with the handpiece, which is designed in this embodiment as a pair of glasses, in particular as filter glasses for the detection of an anomaly on a tooth.

The first embodiment of the medical or dental system 1, shown in FIG. 1, comprises a drive unit and/or control unit 12 with a medical, in particular a dental handpiece 5 and an accessory 34 designed for the operation with the handpiece 5. The accessory in this case is constructed as glasses 34, in particular filter glasses for the detection of an anomaly on a tooth.

The drive unit and/or control unit 12 comprises a housing 13 with a handpiece holder 17. On the front, the drive unit and/or control unit 12 has an operating unit 14. This is formed by a display 15 with a plurality of operating elements 16 for displaying and adjusting the operating parameters of the drive unit and/or control unit 12 and/or of the medical handpiece 5. Furthermore, the drive unit and/or control unit 12 has a fluid tank 18. Finally, in order to drive, control and/or supply the medical handpiece 5 with spray air and/or spray water for cooling or with electrical energy, it is connected via a supply line 19 with the drive unit and/or control unit 12.

The handpiece 5 itself is formed by a handle part 6. Preferably a drive is disposed within the handle part 6 to drive the tool 87. In addition to the drive, the handpiece 5 has a light source 7. Preferably, this is ring-shaped and comprises at least one first light-emitting diode for the illumination of the treatment site and at least a second light-emitting diode for detection of an anomaly at a treatment site. The at least one second light-emitting diode preferably emits electromagnetic radiation, which comprises one or more wavelengths ranging from about 380 nm to 420 nm. The at least two light-emitting diodes are optionally controllable, in particular they can be activated, by the drive unit and/or control unit 12, so that light source 7 can be used either to illuminate the treatment site or to detect an anomaly.

The accessory, which is formed as glasses 34, in particular, as filter glasses, comprises two filters 88, 99, which are designed to allow radiation, emitted from the tooth to be examined to pass through, the wavelength of the radiation being suitable for detecting an anomaly on a tooth. The filters 88, 89 are held in a holder 36 of the glasses frame 35 of filter glasses 34. In addition to holder 36, the glasses 34 comprise two temples 38, 39 and a support 37 for fastening the filters 88, 89 on a user.

For the automatic selection of the at least one first light-emitting diode of the light source 7 for illuminating the treatment site or the at least one second light-emitting diode, which is used in conjunction with filter glasses 34 for detecting an anomaly on a tooth, the medical system 1 has a first transmitting and/or receiving unit 74 and a second transmitting and/or receiving unit 77. The first transmitting and/or receiving unit 74 is located in the filter glasses 34, in particular in the temple 39 or in the holder 37, and the second transmitting and/or receiving unit 77 is located in the handle part 6 of handpiece 5. Both units, the first as well as the second transmitting and/or receiving units 74, 77 are designed for the capacitive coupling of electrical signals $C_1$, $C_2$ into and/or out of the human body 81. Therefore, if both units 74, 77, in particular the filter glasses 34 and handpiece 5, are coupled to the human body 81 of the user, an electrical path 82 for the transmission of electrical signals between the first transmitting and/or receiving unit 74 and the second transmitting and/or receiving unit 77 can be established. Signals received by the second transmitting and/or receiving unit 77 disposed in handpiece 5 are preferably forwarded through the supply line 19 to the drive unit and/or control unit 12, in particular to its control circuit. If the drive unit and/or control unit 12 thus receives at least one electrical signal from the first transmitting and/or receiving unit 74 of the filter glasses 34 (the user wears filter glasses 34 while performing the treatment), said unit automatically activates the at least one second light-emitting diode for detecting an anomaly on a tooth. If no signal is received (the user has taken off the filter glasses 34), the drive unit and/or control unit 12 automatically activates the at least one first light-emitting diode for illuminating the treatment site. Manual switching between the at least one first and at least one second light-emitting diode is therefore no longer necessary.

Figures 1A, 1B:
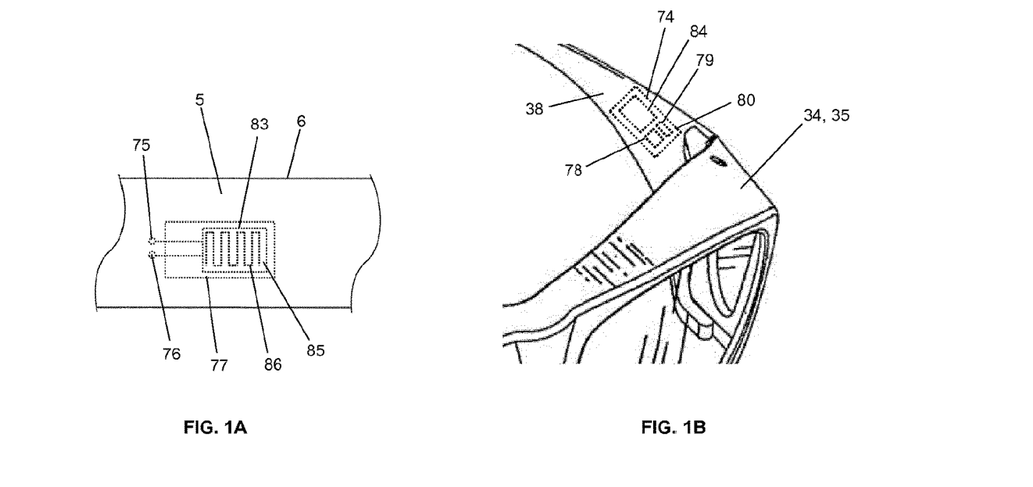
FIG. 1A shows a cutaway view of the medical or dental handpiece in FIG. 1.
FIG. 1B shows a cutaway view of the accessory for the operation with the handpiece, in particular of the glasses of FIG. 1.

FIG. 1A shows a cutaway view of the medical handpiece 5 of FIG. 1 with the second transmitting and/or receiving unit 77. The transmitting and/or receiving unit 77, disposed in the handle part 6, preferably is made up of a printed circuit board 83 for generating and/or receiving electromagnetic fields. The printed circuit board 83 itself preferably has an electrically insulated base body 85 and at least one strip conductor 86. The base body 85 preferably is formed of a flexible carrier material, in particular by a carrier film. To supply the printed circuit board 83 with electrical energy and/or to output received and/or transmitted electrical signals, the transmitting and/or receiving unit 77 has at least two electrical contacts 75, 76. Furthermore, the printed circuit board 83 preferably is disposed in the handle part 6 in such a way, that it can be coupled capacitively with a user and/or with a person to be treated. To this end, it is preferably disposed on the inside or outside of handle part 6. The handle part 6 itself preferably is fabricated from a magnetically and electrically non-conductive material, in particular from plastic, glass, or ceramic.

FIG. 1B shows a cutaway view of the filter glasses 34 of FIG. 1. In the frame 35 of the filter glasses 34, in particular in the temple 38, the first transmitting and/or receiving unit 74 is disposed, so that it can he capacitively coupled to the user. The first transmitting and/or receiving unit 74, just like the second transmitting and/or receiving unit 77, comprises a printed circuit board 84 for generating and/or receiving electromagnetic fields. To supply the printed circuit board 84 with electrical energy, the first transmitting and/or receiving unit 74 has at least one energy storage system 78. A memory unit 79 is used for the storage and/or output of electrical signals and/or data. The transmitting and/or receiving unit 74 preferably is located in a housing 80, the housing 80 being designed in such a way that the functionality of the transmitting and/or receiving unit 74 can be maintained even after multiple cleaning, care and/or sterilization processes. The printed circuit board 84, the energy storage system 78 and the memory unit 79 preferably are housed in a plastic housing 80 by means of an injection molding process. Alternatively, housing 80 can consist of glass or ceramic.

Figure 2:
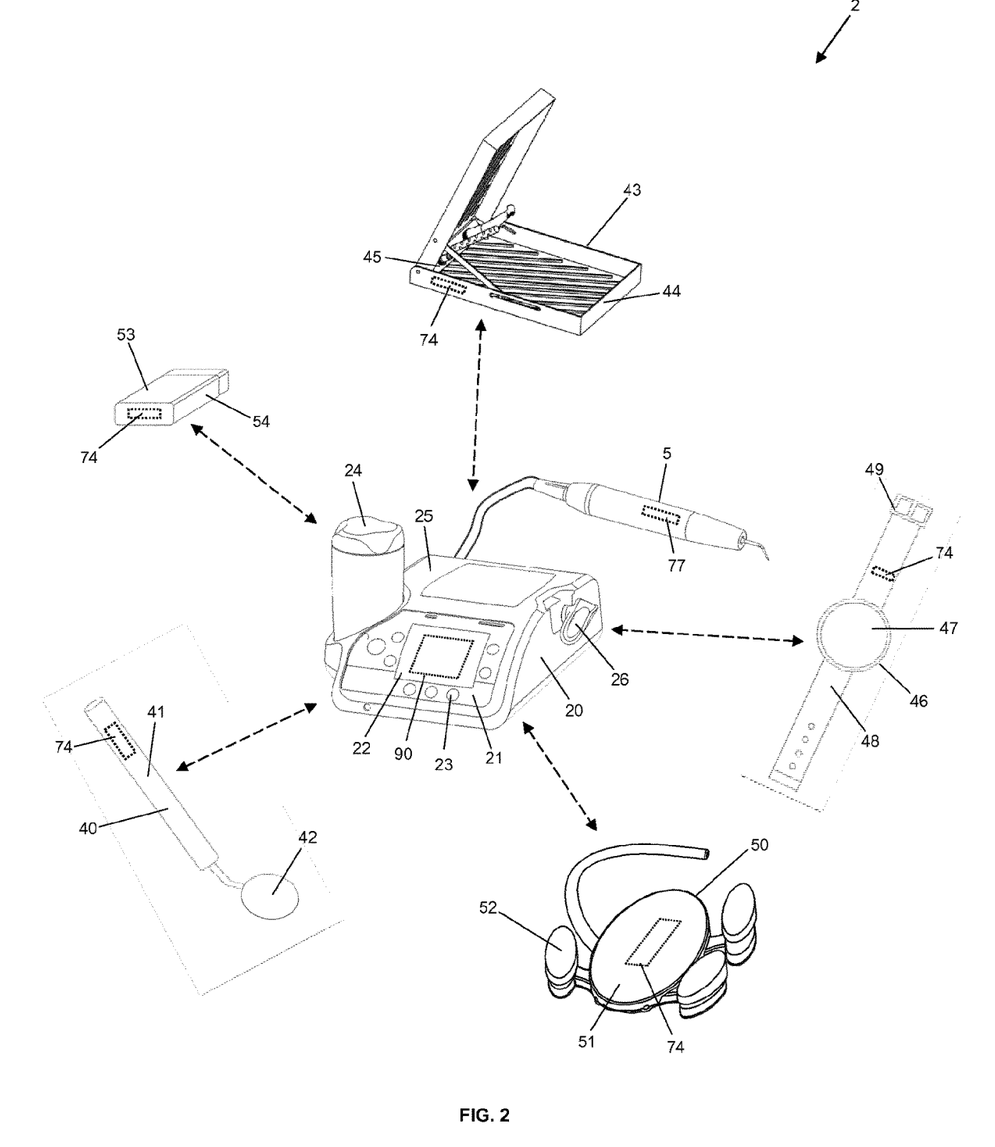
FIG. 2 shows a second embodiment of the medical or dental system with a medical or dental handpiece, a drive unit and/or control unit, and with multiple embodiments of the accessory designed for the operation with the handpiece.

To connect the first transmitting and/or receiving unit 74 detachably with the medical system, in particular with the filter glasses 34, an alternative embodiment of the housing 80 of the first transmitting and/or receiving unit 74 comprises a holding device, in particular a thread, a clip, a clamp, and/or another type of retaining element FIG. 2 shows a second embodiment of the medical, in particular the dental system 2 with at least one medical, in particular dental handpiece 5 and a drive unit and/or control unit 20. Furthermore, there are shown several examples of the accessory designed for the operation with the handpiece 5 and/or for the operation with the drive unit and/or control unit 20. For example, the accessory comprises a hand mirror 40, instrument holder 43, display unit 46, foot pedal 50, and identification dement 53 for user identification and comprises a first transmitting and/or receiving unit 74 in each case.

The drive unit and/or control unit 20 comprises a housing 25 with a handpiece holder 26 and a fluid tank 24. The at least one medical handpiece 5 with the second transmitting and/or receiving unit of FIG. 1 can be coupled to its backside via a supply hose. On the front side, the drive unit and/or control unit 20 comprises a second embodiment of the operating unit 21. In addition to a display 22 and at least one operating element 23, unit 21 comprises a third transmitting and/or receiving unit 90 for capacitively coupling electrical signals into and/or out of the human body 81. The transmitting and/or receiving unit 90 here preferably is integrated into display 22, which itself is preferably designed as a touch screen. Both the second transmitting and/or receiving unit 77 of the handpiece 5, as well as the third transmitting and/or receiving unit 90 of the drive unit and/or control unit 20 are connected to the control circuit of unit 20.

The first embodiment of the accessory comprises a hand mirror 40 with a handle part 41 and a mirror element 42 fastened thereto. The first transmitting and/or receiving unit 74 is preferably disposed in the handle part 41. When the hand mirror 40 and the handpiece 5 and/or the drive unit and/or control unit 20 are coupled to the human body 81 of the user, an electric path is established and electric signals can be transmitted between the first transmitting and/or receiving unit 74 and the second and/or third transmitting and/or receiving unit 77, 90. Thus, for example. if the transmitting and/or receiving unit 90 in the drive unit and/or control unit 20 or the transmitting and/or receiving unit 77 in the handpiece 5 receives at least one electrical signal from the transmitting and/or receiving unit 74 of the hand mirror 40, the control circuit of unit 20 activates the at least one straight handpiece or contra-angled handpiece 5, preferably automatically, and in particular the drive thereof. Thus, an automatic start and stop function for the straight handpiece or contra-angled handpiece 5 is made possible. Manual actuation of the straight handpiece or contra-angled handpiece 5, preferably by means of an on or off switch, is not necessary. Furthermore, through the transmission of electrical signals and/or data the drive unit and/or control unit 20 detects that a user is present, so that further functions, such as for example changing the drive unit and/or control unit 20 from an idle state to an active mode, can be implemented.

The second example of the accessory comprises an instrument holder 43. This comprises, in addition to a housing 44, at least one connecting device 45 with at least one coupling element to hold the at least one medical straight handpiece or contra-angled handpiece 5 and/or a tool. Preferably, the connecting device 45 is mounted pivotably in the housing 44. The first transmitting and/or receiving unit 74 preferably is disposed in the housing 44 of the instrument holder 43. Electrical signals and/or data, preferably operating parameters of the at least one straight handpiece or contra-angled handpiece 5 or tool held in the instrument holder 43, can thereby be transmitted between the first transmitting and/or receiving unit 74 of the instrument holder 43 through the human body of the user to the second transmitting and/or receiving unit 77 of handpiece 5 coupled to the body or to the third transmitting and/or receiving unit 90 of the drive unit and/or control unit 20. When the second and/or third transmitting and/or receiving unit 77, 90 in the drive unit and/or control unit 20 or in the handpiece 5 receives electrical signals and/or data, in particular the operating parameters from the first transmitting and/or receiving unit 74 of the instrument holder 43, the drive unit and/or control unit 20, in particular the control circuit thereof, automatically adjusts the operating parameters for the at least one straight handpiece or contra-angled handpiece 5 and/or tool assigned to the instrument holder 43.

A further example of the accessory comprises a display unit 46, which preferably takes the form of a watch (or other wearable device). In addition to a display 47, the display unit 46 has a wrist strap 48 with a fastening element 49 to permit it to be connected preferably to an arm of the user. The first transmitting and/or receiving unit 74 preferably is located in the wrist strap 48 and electrically connected with the display 47. Electrical signals and/or data, preferably detected and/or adjusted parameters of the straight handpiece or contra-angled handpiece 5 and/or of the drive unit and/or control unit 20, can thereby be transmitted from the transmitting and/or receiving unit 77 of the handpiece 5 or from the transmitting and/or receiving unit 90 of the drive unit and/or control unit 20 through the human body of the user to the transmitting and/or receiving unit 74 and display 47 of the display unit 46. This permits displaying detected and/or adjusted parameters of the straight handpiece or contra-angled handpiece 5 and/or of the drive unit and/or control unit 20 directly in the treatment area of the user.

The fourth embodiment of the accessory comprises a foot pedal 50 for the drive unit and/or control unit 20. The foot pedal 50 preferably serves to activate an electric drive in the handpiece 5, which is controlled by the control circuit in the drive unit and/or control unit 20. The foot pedal 50 comprises at least one pedal 51 as well at least one operating element 52. The pedal 51 preferably is used to regulate variable parameters, such as different speeds, and the operating element 52 is used to turn on and off the foot pedal 50 and/or to switch between the different variable parameters. When actuated, both elements, the pedal 51 and the operating element 52, send electrical signals to a control unit in the foot pedal 50, which in turn is connected to the first transmitting and/or receiving unit 74. The transmitting and/or receiving unit 74 preferably is located in pedal 51. Alternatively, it can also be positioned in the at least one operating element 52. Electrical signals and/or data, such as rotational speed values, can thereby be transmitted from the transmitting and/or receiving unit 74 of the foot pedal 50 through the human body of the user to the second transmitting and/or receiving unit 77 in the medical handpiece 5 and/or to the third transmitting and/or receiving unit 90 in the drive unit and/or control unit 20. The control circuit of the drive unit and/or control unit 20 thus activates the electrical drive in the handpiece 5 as a function of the signals and/or of the data received from the foot pedal 50. Furthermore, the first transmitting and/or receiving unit 74 of foot pedal 50 can also receive electrical signals and/or data, so that the at least one foot pedal 51 can be assigned to several drive unit and/or control units.

The fifth embodiment of the accessory comprises an identification element 53. Element 53 comprises a housing 54, in which the first transmitting and/or receiving unit 74 is disposed. The identification element 53 is used to identify the user of the medical system 2, in particular for the automatic selection of operating programs and/or operating parameters in the drive unit and/or control unit 20. Electric signals and/or data, such as user codes, can be transmitted from the first transmitting and/or receiving unit 74 of identification element 53 through the human body of the user to the second transmitting and/or receiving unit 77 in the medical handpiece 5 and/or to the third transmitting and/or receiving unit 90 of the drive unit and/or control unit 20. The drive unit and/or control unit 20 thus automatically sets up the operating programs and/or operating parameters as a function of the signals and/or data received.

Figure 3:
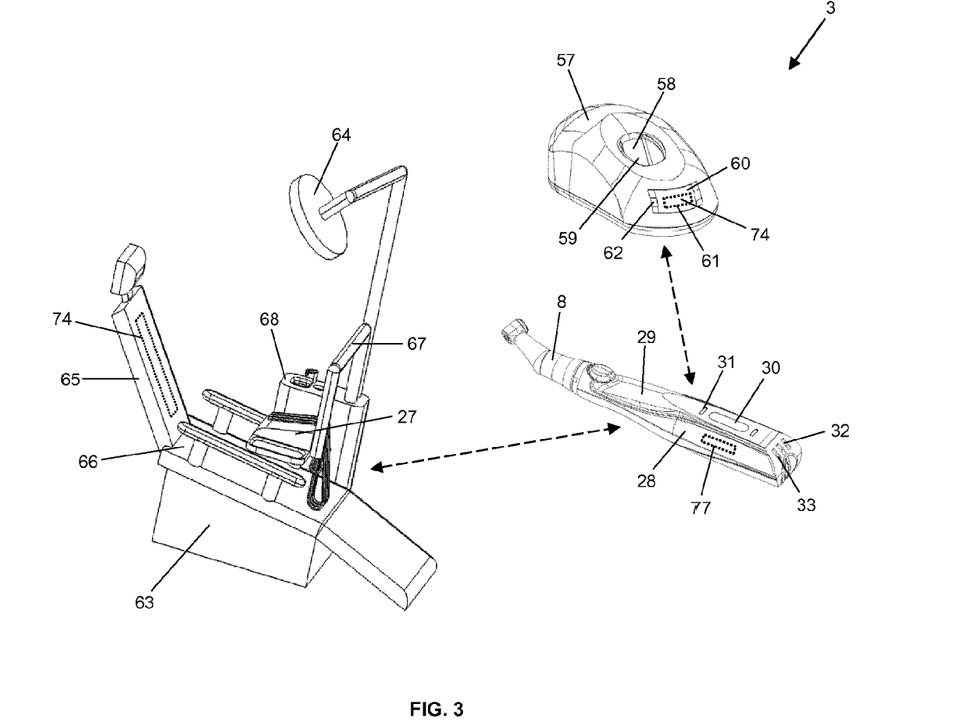
FIG. 3 shows a third embodiment of the medical or dental system with a medical or dental contra-angle handpiece and a, in particular wireless, drive unit and/or control unit which can be coupled to the contra-angle handpiece, a base unit, as well as a second drive unit and/or control unit, which is in particular integrated into a treatment unit.

FIG. 3 shows a third example of the medical, in particular the dental system 3 with a medical, in particular a dental contra-angle handpiece 8 and a first, especially cordless drive unit and/or control unit 28, which can be connected to the contra-angle handpiece 8, a base station (or unit) 57, as well as a second drive unit and/or control unit 27, which in particular is disposed in or at a treatment unit 63.

The preferably cordless drive unit and/or control unit 28 which can be connected to contra-angle handpiece 8 has a housing 29, in which a control circuit is disposed for controlling a drive, in particular, an electric motor accommodated in the drive unit and/or control unit 28. In addition to the drive, the unit 28 preferably has at least one energy storage system for supplying the drive and/or the control circuit with electrical energy, as well as at least one data memory for storing data. On the backside of the housing 29 the drive unit and/or control unit 28 has at least two charging contacts 32, 33 for the energy storage system. For the display and adjustment of detected and/or preset operating parameters and/or operating programs of the drive disposed in the drive unit and/or control unit 28 and/or of the connectable contra-angle handpiece 8, the drive unit and/or control unit 28 has a display 30 as well as at least one operating element 31.

To receive preset operating programs and/or operating parameters from a first transmitting and/or receiving unit 74, which preferably is disposed in the base station 57 or in the drive unit and/or control unit 27 of treatment unit 63, the drive unit and/or control unit 28 comprises a second transmitting and/or receiving unit 77. The second transmitting and/or receiving unit 77 is designed for receiving and transmitting signals and/or data in order to transmit measured operating parameters of the drive and/or the contra-angle handpiece 8 to the base station 57 and/or to the treatment unit 63. Both units, the first transmitting and/or receiving unit 74 and the second transmitting and/or receiving unit 77, are designed for the capacitive coupling of electrical signals into and/or out of the human body. If, for example, the drive unit and/or control unit 28, the base station 57, and/or the treatment device 63 are coupled to the human body 81 of the user, electrical signals and/or data can be transmitted between the first transmitting and/or receiving unit 74 and the second transmitting and/or receiving unit 77.

The first transmitting and/or receiving unit 74 of the base station 57, which has a holder 58 and a charger 59 for the drive unit and/or control unit 28, is therefore preferably disposed in or at a display 61 of an operating unit 60 with at least one operating element 62 of the base station 57 and connected with a memory unit located in the base station 57 on which operating programs and/or operating programs can be stored. The display 61 in this example preferably is also implemented as a touch screen. Electrical signals and/or data, in particular operating parameters and/or operating programs, can hereby be transmitted during user selection using the touch screen 60 from the memory unit of the base unit 57 to the drive unit and/or control unit 28. At the same time, operating parameters detected by the drive unit and/or control unit 28 can be stored on the memory unit of the base station 57.

The transmitting and/or receiving unit 74 of the second drive unit and/or control unit 27 preferably is disposed in or at the backrest 65 and/or in or at the seating and/or reclining surface 66 for the person to be treated in the treatment unit 63 and connected with the second transmitting and/or receiving unit 27. In addition to the second drive unit and/or control unit 27 and the seating and/or reclining surface 66, the treatment unit 63 comprises an illumination system 64, a sink 68 and a supply line 67. The supply lead 67 serves, among other things, to supply the drive unit and/or control unit 27 with electrical energy. To transmit electrical signals and/or data between the second drive unit and/or control unit 27 and the wireless drive unit and/or control unit 28, the first transmitting and/or receiving unit 74 in the backrest 65 and the second transmitting and/or receiving unit 77 in the drive unit and/or control unit 28 are designed for the capacitive coupling of electrical signals into and/or out of the human body and are disposed in the backrest 65 and drive unit and/or control unit 28 in such a way that they can be coupled with the human body of the patient. To this end, the second transmitting and/or receiving unit 77 in the wireless drive unit and/or control unit 28 preferably is designed in such a way, that the electric signals and/or data, in particular the electromagnetic fields generated, can be coupled with the human body of the patient, even when the latter does not touch or contact the second transmitting and/or receiving unit 77 directly. Transmission of the electrical signals and/or data is contact-free here. Furthermore, the arrangement shown in FIG. 4 permits electrical signals and/or data to be transmitted from the drive unit and/or control unit 27 through the wireless drive unit and/or control unit 28 to the base station 57.

Figure 4:
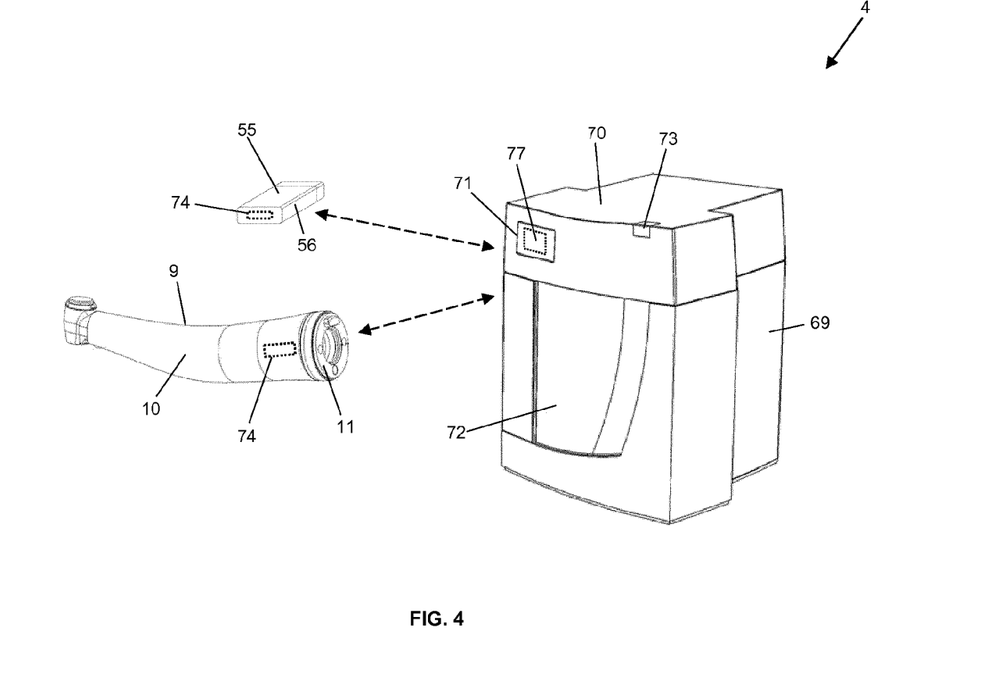
FIG. 4 shows a fourth embodiment of the medical or dental system with a processing device for processing a medical or dental straight handpiece or contra-angled handpiece and an accessory designed for the operation with the processing device.

FIG. 4 shows a fourth example of the medical or dental system 4 with a processing device 69 for the processing of a medical or a dental straight handpiece or contra-angled handpiece 9 and an accessory 55 designed for the operation with the processing device. The processing device 69 preferably is constructed in the form of a sterilizer, in particular of a steam sterilizer. The sterilizer comprises a housing 70 with several outer walls. One outer wall, in particular a side wall, preferably forms the operating side of the processing device 69. The latter preferably comprises at least one operating unit 71 and at least one operating element 73, which are used particular to select different operating programs or to set operating parameters and are connected to a control device to control and/or regulate the processing process. In addition to the operating unit 71, the housing 70 of the sterilizer comprises an opening that is connected to a processing chamber of the sterilizer. Through the opening, a straight handpiece or contra-angled handpiece 9 or a medical accessory to be processed or cleaned can be introduced into or taken out of the processing chamber. The opening can be closed off by means of a door 72 which is preferably mounted rotatably through a hinge relative to the several walls of the sterilizer. Preferably, a media feed line to supply the at least one straight handpiece or contra-angled handpiece 9 which is held in the processing chamber with a cleaning and/or care agent is arranged in the processing chamber.

For the automatic selection of different operating programs or operating parameters as well as for identifying the user, the medical system 4 comprises at least one first transmitting and/or receiving unit 74 and at least one second transmitting and/or receiving unit 77. The first transmitting and/or receiving unit 74 is disposed in the at least one medical contra-angle handpiece 9, which is to be processed, in particular in or at the handle part 10 thereof, and/or in the accessory 55 designed for the operation with the processing device 69, in particular designed as an identification element, and preferably in the housing 56 thereof. At its rear end the contra-angle handpiece 9 preferably comprises a coupling element 11 for coupling the contra-angle handpiece 9 to the processing device 69, in particular to its media feed. The second transmitting and/or receiving unit 77 in this example is disposed in or at the operating unit 71 of processing device 69. Alternatively, it may be disposed in or at the operating element 73 or in or at the door 72 of the processing device 69.

Also in this embodiment, both the first transmitting and/or receiving unit 74 and the second transmitting and/or receiving unit 77 are designed for the capacitive coupling of electrical signals into and/or out of the human body. If the first transmitting and/or receiving unit 74 and the second transmitting and/or receiving unit 77, in particular of the at least one contra-angle handpiece 9, of the identification element 55 and of the processing device 69, are coupled to the human body 81 of the user, an electrical path 82 is established for the transmission of electrical signals between the at least two transmitting and/or receiving units 74, 77. Electrical signals sent from the first transmitting and/or receiving unit 74 of the medical contra-angle handpiece 9 contain, in particular, the serial number of the contra-angle handpiece 9 and/or the operating parameters for the processing device 69. The transmitting and/or receiving unit 74 of the identification element 55 preferably transmits a user code to identify the user. The second transmitting and/or receiving unit 77 receives the electrical signals sent by the first transmitting and/or receiving unit 74 and preferably forwards them to the control device of the processing device 69. In this way, operating parameters and/or operating programs are selected automatically depending on the contra-angled handpieces 9 to be processed. Furthermore, by receiving user codes, the user of the processing device 69 is assigned to the processed straight handpiece or contra-angled handpieces 9. Manual input of user data and/or operating parameters for the contra-angle handpiece 9 to be cleaned, is thereby no longer necessary.

The invention is not limited to the embodiments described, but comprises all embodiments, which employ or include the basic, analogous functional principle of the invention. Furthermore, all the features of all the embodiments described and shown can be combined with one another.

What is claimed is:
1. A medical or dental system comprising:
at least one first transmitting and/or receiving unit, wherein the first transmitting and/or receiving unit is disposed in an identification element, wherein the identification element is assigned to a user and comprises an identification code that identities the user;
a medical or dental processing device for cleaning, disinfecting and/or sterilizing comprising a housing having an outer wall with an opening that connects to a processing chamber and through which a medical or dental device to be cleaned, disinfected and/or sterilized can be introduced into or removed therefrom, a door for closing the opening and at least one second transmitting and/or receiving unit disposed in or at the outer wall with the opening that connects to a processing chamber or in or at the door for closing the opening;
wherein the first transmitting and/or receiving unit is configured for capacitive coupling of electrical signals or data into a body of the user so that an electrical path which extends through the body of the user can be established for transmission of electrical signals or data between the first transmitting and/or receiving unit and the second transmitting and/or receiving unit which is configured for capacitive coupling of electrical signals or data out of the body of the user;
wherein the electrical signals or data comprise the identification code that identities the user, and wherein the first transmitting and/or receiving unit is configured at least for sending the electrical signals or data comprising the identification code from the identification element along the electrical path, and wherein the second transmitting and/or receiving unit is configured at least for receiving the identification code from the electrical path to identify the user.

2. The medical or dental system according to claim 1, wherein the first transmitting and/or receiving unit and the second transmitting and/or receiving unit each comprises at least one printed circuit board having an insulated base body and having at least one electrical conductor for generating and/or receiving electromagnetic fields which can be coupled into and/or out of the body of the user.

3. The medical or dental system according to claim 2, wherein the base body of the printed circuit board comprises a flexible carrier material.

4. The medical or dental system according to claim 2, wherein at least one of the first transmitting and/or receiving unit and the second transmitting and/or receiving unit comprises at least two electrical contacts to supply the printed circuit board with electrical energy and/or to emit electrical signals or data.

5. The medical or dental system according to claim 1, wherein at least one of the first transmitting and/or receiving unit and/or the second transmitting and/or receiving unit comprises at least one energy storage system to supply the respective transmitting and/or receiving unit with electrical energy.

6. The medical or dental system according to claim 1, further comprising at least one memory unit to store and/or output data.

7. The medical or dental system according to claim 1, wherein the second transmitting and/or receiving unit is disposed adjacent or at an actuating and/or operating element of the processing device for cleaning, disinfecting, and/or sterilizing.

8. The medical or dental system according to claim 1, wherein the medical or dental processing device for cleaning, disinfecting and/or sterilizing comprises one of a sterilizer or a steam sterilizer.

9. The medical or dental system according to claim 1, wherein the second transmitting and/or receiving unit is configured to receive the electrical signals or data comprising the identification code and to forward them to a control device of the processing device for cleaning, disinfecting, and/or sterilizing.

10. A method of using the medical or dental system of claim 1, comprising:
positioning the at least one first transmitting and/or receiving unit in contact with or in close proximity to the body of the user;
positioning the at least one second transmitting and/or receiving unit in operative relation with the first transmitting and/or receiving unit;
capacitively coupling the first transmitting and/or receiving unit with the second transmitting and/or receiving unit through contact with or close proximity of the user's body to the second transmitting and/or receiving unit;
communicating electrical signals and/or data between the capacitively coupled first and second transmitting and/or receiving units, the electrical signals and/or data comprising at least an identification of the user automatically transmitted to a device with which the second transmitting and/or receiving device is associated.

11. A medical or dental system comprising:

a transmitting and/or receiving unit of a processing device for cleaning, disinfecting and/or sterilizing disposed at an actuating or operating element of the processing device to select different operating programs or to set operating parameters, wherein the actuating or operating element is arranged on an outer wall of the medical or dental processing device having an opening that connects to a processing chamber and through which a medical or dental device to be cleaned, disinfected and/or sterilized can be introduced into or taken out of the processing chamber, a remote transmitting and/or receiving unit at a handle part or gripping part of a medical or dental handpiece configured for capacitive coupling of electrical signals or data into a human body, wherein the transmitting and/or receiving unit of the processing device is configured for capacitive coupling of electrical signals or data out of a human body, so that an electrical path which extends through a body of a user from one hand of the user holding the handle part or gripping part of the medical or dental handpiece to the other hand of the user touching the transmitting and/or receiving unit of the processing device can be established for the transmission of electrical signals or data between the transmitting and/or receiving unit of the processing device, through the body and the remote transmitting and/or receiving unit of the medical or dental handpiece located remote from the processing device, to transmit the electrical signals or data along the electrical path.

12. The medical or dental system according to claim 11, wherein the outer wall on which the actuating or operating element is arranged is part of a housing.

13. The medical or dental system according to claim 11, wherein the actuating or operating element is configured for selection of different operating programs or the setting of operating parameters.

14. The medical or dental system according to claim 11, wherein the remote transmitting and/or receiving unit of the medical or dental handpiece is configured to transmit electrical signals or data comprising at least one of a serial number of the medical or dental handpiece and an operating parameter for the processing device via the body to the processing device for cleaning, disinfecting and/or sterilizing.

15. The medical or dental system according to claim 11, wherein the remote transmitting and/or receiving unit of the medical or dental handpiece is further configured for capacitive coupling of electrical signals or data out of a human body and the transmitting and/or receiving unit of the processing device is further configured for capacitive coupling of electrical signals or data into a human body.

16. The medical or dental system according to claim 11, wherein the transmitting and/or receiving unit of the processing device for cleaning, disinfecting and/or sterilizing is configured to receive the electrical signals or data sent by the remote transmitting and/or receiving unit of the medical or dental handpiece and to forward them to a control device of the processing device, wherein the control device is configured to automatically select operating parameters and/or operating programs of the processing device for cleaning, disinfecting and/or sterilizing depending on the electrical signals or data sent by the remote transmitting and/or receiving unit of the medical or dental handpiece to be processed.

17. The medical or dental system according to claim 11, wherein the medical or dental processing device for cleaning, disinfecting and/or sterilizing comprises one of a sterilizer or a steam sterilizer.

18. A medical or dental system comprising:
an identification element having a first transmitting and/or receiving unit, wherein the identification element comprises an identification code that identifies a user;
a medical or dental processing device for cleaning, disinfecting and/or sterilizing having a processing chamber, an opening in an outer wall of the medical or dental processing device that connects to the processing chamber and through which a medical or dental device to be cleaned, disinfected and/or sterilized can be introduced into or taken out of the processing chamber, a door for closing the opening, a media feed line configured to supply a cleaning and/or care agent to a medical or dental device to be cleaned, disinfected and/or sterilized which is in the processing chamber, and a second transmitting and/or receiving unit;
wherein the first transmitting and/or receiving unit is configured for capacitive coupling of the identification code that identifies the user into a body of the user and wherein the second transmitting and/or receiving unit is disposed in or at the outer wall with the opening that connects to a processing chamber or in or at the door for closing the opening and is configured for capacitive coupling of the identification code that identifies the user out of the body of the user through a user's hand when the user touches the outer wall with the opening that connects to a processing chamber or the door with the user's hand, so that an electrical path which extends through the body and the user's hand can be established between the first transmitting and/or receiving unit and the second transmitting and/or receiving unit for capacitive transmission of the identification code that identifies the user from the first transmitting and/or receiving unit to the second transmitting and/or receiving unit.

19. The medical or dental system according to claim 18, wherein the second transmitting and/or receiving unit is configured to receive the identification code and to forward it to a control device of the processing device for cleaning, disinfecting, and/or sterilizing, wherein the control device is configured to assign the user of the processing device to the cleaned, disinfected and/or sterilized medical or dental device.

20. The medical or dental system according to claim 18, wherein the medical or dental processing device for cleaning, disinfecting and/or sterilizing comprises one of a sterilizer or a steam sterilizer.

21. A method of using a medical or dental system, the medical or dental system comprising:
at least one first transmitting and/or receiving unit, wherein the first transmitting and/or receiving unit is disposed in an identification element, wherein the identification element is assigned to a user and comprises an identification that identifies the user,
a medical or dental processing device for cleaning, disinfecting and/or sterilizing comprising a housing having an outer wall with an opening that connects to a processing chamber and through which a medical or dental device to be cleaned, disinfected and/or sterilized can be introduced into or removed therefrom, a door for closing the opening, and
at least one second transmitting and/or receiving unit disposed in or at the outer wall with the opening that connects to a processing chamber or in or at the door for closing the opening,
the method comprising:
positioning the at least one first transmitting and/or receiving unit in contact with or in close proximity to the body of the user;
positioning the at least one second transmitting and/or receiving unit in operative relation with the first transmitting and/or receiving unit;
capacitively coupling the first transmitting and/or receiving unit with the second transmitting and/or receiving unit through contact with or close proximity of the body of the user to the second transmitting and/or receiving unit; and
communicating electrical signals and/or data between the capacitively coupled first and second transmitting and/or receiving units, the electrical signals and/or data comprising at least the identification that identifies the user being communicated to the medical or dental processing device for cleaning, disinfecting and/or sterilizing.

* * * * *